(12) United States Patent
Elazizi et al.

(10) Patent No.: US 9,642,942 B2
(45) Date of Patent: May 9, 2017

(54) OSTEOGENIC REGENERATIVE SCAFFOLD MATRIX COMPOSITION

(71) Applicants: Mohamad Elazizi, Weston, FL (US); Peter Murray, Davie, FL (US); H. Thomas Temple, Miami, FL (US)

(72) Inventors: Mohamad Elazizi, Weston, FL (US); Peter Murray, Davie, FL (US); H. Thomas Temple, Miami, FL (US)

(73) Assignee: Nova Southeastern University, Fort Lauderdale, FL (US)

( * ) Notice: Subject to any disclaimer, the term of this patent is extended or adjusted under 35 U.S.C. 154(b) by 0 days.

(21) Appl. No.: 14/800,770

(22) Filed: Jul. 16, 2015

(65) Prior Publication Data

US 2017/0014550 A1    Jan. 19, 2017

(51) Int. Cl.
| | | |
|---|---|---|
| *A61F 5/00* | (2006.01) | |
| *A61P 19/00* | (2006.01) | |
| *A61P 29/00* | (2006.01) | |
| *A61L 27/54* | (2006.01) | |
| *A61L 27/18* | (2006.01) | |
| *A61L 27/26* | (2006.01) | |
| *A61L 27/24* | (2006.01) | |
| *A61L 27/22* | (2006.01) | |
| *A61L 27/10* | (2006.01) | |
| *A61L 27/36* | (2006.01) | |
| *A61L 27/12* | (2006.01) | |
| *A61F 2/28* | (2006.01) | |

(Continued)

(52) U.S. Cl.
CPC ............ *A61L 27/54* (2013.01); *A61F 2/2846* (2013.01); *A61L 27/10* (2013.01); *A61L 27/12* (2013.01); *A61L 27/18* (2013.01); *A61L 27/225* (2013.01); *A61L 27/24* (2013.01); *A61L 27/26* (2013.01); *A61L 27/365* (2013.01); *A61L 27/3608* (2013.01); *A61L 27/56* (2013.01); *A61L 27/58* (2013.01); *A61F 2002/2817* (2013.01); *A61F 2002/2835* (2013.01); *A61L 2430/02* (2013.01)

(58) Field of Classification Search
None
See application file for complete search history.

(56) References Cited

FOREIGN PATENT DOCUMENTS

WO    WO 2009/129316 A2 * 10/2009

\* cited by examiner

*Primary Examiner* — Elizabeth C Kemmerer
(74) *Attorney, Agent, or Firm* — David L. King

(57) ABSTRACT

The implantable scaffold matrix composition for osteogenic regeneration has a biodegradable polymer material selected from the group consisting of one or more of polylactic acid, polyglycolic acid, or polycaprolactone, or any combination thereof to provide a time release delivery of an osteogenic effect and further has a pharmaceutical composition selected from the group consisting of one or more of ibuprofen, non-steroidal anti-inflammatory drugs (NSAIDS), acetaminophen, or naproxen sodium or any combination thereof and wherein the implantable composition has a primary and a secondary time release. The primary time release being one of the polymer compositions; each time release extending occurring between 0 days and 19 days, both not being at 0 days. In a preferred composition, the scaffold has an organic material for inhibiting osteoclast selected from a group consisting of one or more of Galardin, Decorin, Actinonin, Marimastat, Batimastat, and phosphodiesterase type 4 or any combination of osteoclast inhibitors.

5 Claims, 8 Drawing Sheets

(51) Int. Cl.
*A61L 27/56* (2006.01)
*A61L 27/58* (2006.01)

OSTEOGENIC REGENERATIVE SCAFFOLD MATRIX COMPOSITION

TECHNICAL FIELD

The present invention is directed to an implantable osteogenic regenerative scaffold matrix composition for use in bone defect repair.

BACKGROUND OF THE INVENTION

Bone and joint disorders caused by autoimmune disease characterized by chronic inflammation and bone destruction because of an abnormal increase in bone resorption by osteoclasts are very common. The most common joint disease is osteoarthritis (OA), it can cause constant pain, suffering, reduced limb function, loss of mobility, and loss of quality of life for 27 million Americans. Americans have a 46% and 25% lifetime risk of developing OA in their knee and hip. One third of older age American women suffer from OA, which is a progressive loss of bone mineral which increases their risk of bone fracture. Trauma, radiation, joint replacements, hip replacements, dental implants, and some drugs can cause osteonecrosis (ON), where areas of bone have died. Unfortunately, despite the high degree of disability and suffering caused to millions of people, there is no cure for OA, osteoporosis (OP), or ON, except to surgically remove the immobile joint and to replace it with an implant. The FDA has approved the use of bone antiresorptive medications to slow the rate of bone loss and anabolics to increase the rate of bone formation, but these have a limited effectiveness and cannot cure OA, OP, or ON. Although bone and joint disorders are more common in middle-age and elderly people, it is not accurate to claim that the joints and bone have "worn out". This is because in healthy individuals, the deposition of bone by osteoblasts is matched by the resorption of bone by osteoclasts. However, when there is an abnormal increase in bone resorption the osteoclasts have become more active and resorbed bone and surrounding soft tissues. Some other immune cell types, such macrophages, and T or B lymphocytes have been reported to be involved in the pathogenesis of chronic inflammation in RA. However, bone destruction is considered to be mainly controlled by enhanced activation of osteoclasts, the only somatic cell type capable of resorbing bone matrices. Therefore, the inventors of the present invention believe the key to preventing the bone resorbing processes of OA, OP, and ON is to block the activity of the osteoclasts.

An osteoclast is a cell which resorbs bone. Osteoclasts are about 150-200 µm in diameter, typically have five nuclei, and a cytoplasm filled with acid phosphatase which can be released to resorb bone. Normal bone homeostasis, bone formation and bone resorption are closely coupled processes involved in the normal remodeling of bone. In OP, the net rate of bone resorption exceeds the rate of bone formation, resulting in a decrease in bone mass without a defect in bone mineralization. In post-menopausal women, osteoclast activity may increase because of a decrease in circulating estrogen after the menopause. Osteoclast activity may also increase in men who suffer a decrease in circulating testosterone. These physiological changes can result in a net loss of bone. The amount of bone available for mechanical support of the skeleton eventually falls below the fracture threshold and a bone fracture can occur with little or no trauma. Osteoclasts can also resorb bone at sites of trauma, implants, materials, infection, and surgery. The osteoblast resorption of bone is a self-perpetuating process, which can only be halted by the surgical removal of the resorbed and adjacent tissues, as well as any materials or implants, traumatized tissues, or infection, which stimulated the osteoclasts. The current inventors therefore believe the ability to halt the bone resorbing activity of the osteoclasts could be beneficial to prevent bone loss, and the disabling and dysfunctional effects it can have on patients.

Particularly devastating is the occurrence of bone resorption by osteoclasts at the site of bone defect repair. Ideally, these inventors believe what is needed is an implantable osteogenic scaffold which can control the osteoblasts, osteoclasts and local inflammatory cells within the site of a bone defect to accomplish its regeneration.

A few inhibitors of collagen degradation have been identified in various cell lines, type 1 collagen is the major organic component of bone. The present inventors found some potential inhibitors of the osteoblast degradation of bone and collagen are; hydroxamate-based matrix metalloproteinase (MMP) inhibitors, thiol-based MMP inhibitors, Pyrimidine-based inhibitors, hydroxypyrone-based MMP inhibitors, phosphorus-based MMP inhibitors, tetracycline-based MMP inhibitors, and endogenous MMP inhibitors also known as tissue inhibitors of metalloproteinases (TIMPs). The names of some of these Galardin, Decorin, Actinonin, Marimastat, Batimastat, Ilomastat, Interleukin-1, oncostatin M, Tanomastat, Cipemastat, Rebimastat, phosphodiesterase type 4 (PDE4) inhibitor, hydroxamate-based MMP inhibitors, MMI-270, MMI-166, ABT-770, RS-130830, compound 239796-97-5, compound 420121-84, compound 544678-85, Compound 556052-30-3, Ro 282653, compound 848773-43-3, compound 3-hydroxypyran-4-one also called 868368-30, metastat (also known as COL-3), Prinomastat, and Gelatinases.

One third of older age American women suffer from OP, which is a progressive loss of bone mineral which increases their risk of bone fracture. After women reach the menopause, there is a sudden drop in their levels of estrogen. The lack of estrogen is a major causal factor of OP, because it causes an increase in the osteoclast degradation of bone, resulting in impaired bone mass and architecture. The U.S. Food and Drug Administration has approved estrogen with progesterone hormone therapy (HT) for post-menopausal women to increase their bone mineral density and to reduce their risk of an OP-related bone fracture. Because of the potential effects of hormones and growth factors on the osteoclast degradation of bone, these inventors believe there is a need to investigate the molecular mechanisms of how estrogen (estradiol), testosterone, progesterone, Gonadotropin-releasing hormone (GnRH), insulin, Granulocyte-macrophage colony-stimulating factor (GM-CSF), Sphingosine-1-phosphate (S1P), Bone morphogenetic proteins 2 and 4 (BMP-2), (BMP-4), Transforming growth factor beta 1 (TGF-β1) can alter the proliferation of osteoclasts, as well as their bone and collagen degradation.

A bone defect can be caused by trauma, tumor, cancer, radiation, drugs, infection, implant surgery, chronic inflammation, or a disease, such as osteoarthritis, osteoporosis, and osteonecrosis. In healthy individuals, the deposition of bone by osteoblasts is matched by the resorption of bone by osteoclasts as reported by Bocanegra-Pérez M S et al in an article entitled, "Bone metabolism and clinical study of 44 patients with bisphosphonate-related osteonecrosis of the jaws" in the Med Oral Patol Oral Cir Bucal. 2012; 17:e948-55. However, when there is an abnormal increase in bone resorption the osteoclasts have become more active and resorb bone and surrounding soft tissues reported by Crotti T N et al in an article entitled, "Factors regulating osteoclast formation in human tissues adjacent to peri-implant bone loss: expression of receptor activator NFkappaB, RANK ligand and osteoprotegerin" in Biomaterials. 2004; 25:565-73.

Osteoclasts are bone-resorbing giant polykaryons that differentiate from mononuclear macrophage/monocyte-lineage hematopoietic precursors as shown by in vivo fluorescence imaging of bone-resorbing osteoclasts. Upon stimulation by cytokines, such as M-CSF and RANK ligand, osteoclast precursor monocytes migrate and attach onto the bone surface. They then fuse with each other to form giant cells (differentiation) and mediate bone resorption.

Definitions

As used herein and in the claims:

"Bone defect" means the absence of bone caused by trauma, tumor, cancer, radiation, drugs, infection, implant surgery, chronic inflammation, or a disease, such as Osteoarthritis, Osteoporosis, and osteonecrosis.

"Osteogenic regeneration" means to control the activity of osteoblasts, osteoclasts, and local inflammatory cells to regenerate bone.

"Biodegradable polymer scaffold" means the material is porous to allow blood carrying osteoblasts and inflammatory cells to populate and eventually resorb the scaffold.

SUMMARY OF THE INVENTION

In this invention, the inventors have disclosed the key to preventing the resorption of bone is to block the activity of the osteoclasts. Some potential inhibitors of the osteoblast degradation of bone and collagen are; hydroxamate-based matrix metalloproteinase (MMP) inhibitors, thiol-based MMP inhibitors, Pyrimidine-based inhibitors, hydroxypyrone-based MMP inhibitors, phosphorus-based MMP inhibitors, tetracycline-based MMP inhibitors, and endogenous MMP inhibitors also known as tissue inhibitors of metalloproteinases (TIMPs). The names of some of these Galardin, Decorin, Actinonin, Marimastat, Batimastat, Ilomastat, Interleukin-1, oncostatin M, Tanomastat, Cipemastat, Rebimastat, phosphodiesterase type4 (PDE4) inhibitor, hydroxamate-based MMP inhibitors, MMI-270, MMI-166, ABT-770, RS-130830, compound 239796-97-5, compound 420121-84, compound 544678-85, Compound 556052-30-3, Ro 282653, compound 848773-43-3, compound 3-hydroxypyran-4-one also called 868368-30, metastat (also known as COL-3), Prinomastat, and Gelatinases.

Many bone defects cannot heal in the absence of surgical intervention and filling with freeze-dried bone. Even though freeze-dried bone has a similar hydroxyapatite and collagen structure as healthy bone, its use has regeneration limitations. The objective of the present invention to provide an osteogenic scaffold which can control the osteoblasts, osteoclasts and local inflammatory cells within the site of a bone defect to accomplish its regeneration.

The implantable osteogenic regenerative scaffold matrix composition for replacing necrotic bone is configured and dimensioned for insertion into a revascularized bone defect. The implantable scaffold matrix composition has a polymer material to promote osteoblast attachment selected from the group consisting of one or more of polylactic acid, polyglycolic acid or polycaprolactone or any combination thereof to provide a time released delivery of an osteogenic effect and further has a pharmaceutical composition selected from the group consisting of one or more of ibuprofen, non-steroidal anti-inflammatory drugs (NSAIDS), acetaminophen, or naproxen sodium or any combination thereof and wherein the implantable composition has a primary and a secondary time release. The primary time release being one or more of the pharmaceutical compositions and the secondary time release being one or more of the polymer compositions; each time release extending and occurring between 0 days and 19 days, both not being at 0 days.

In a preferred composition, further has an organic material for inhibiting osteoclast selected from a group consisting of one nor more of hydroxamate-based matrix metalloproteinase (MMP) inhibitors, thiol-based MMP inhibitors, Pyrimidine-based inhibitors, hydroxypyrone-based MMP inhibitors, phosphorus-based MMP inhibitors, tetracycline-based MMP inhibitors, and endogenous MMP inhibitors also known as tissue inhibitors of metalloproteinases (TIMPs). The names of some of these Galardin, Decorin, Actinonin, Marimastat, Batimastat, Ilomastat, Interleukin-1, oncostatin M, Tanomastat, Cipemastat, Rebimastat, phosphodiesterase type 4 (PDE4) inhibitor, hydroxamate-based MMP inhibitors, MMI-270, MMI-166, ABT-770, RS-130830, compound 239796-97-5, compound 420121-84, compound 544678-85, Compound 556052-30-3, Ro 282653, compound 848773-43-3, compound 3-hydroxypyran-4-one also called 868368-30, metastat (also known as COL-3), Prinomastat, and Gelatinases, or any combination of the osteoclast inhibitors.

BRIEF DESCRIPTION OF THE DRAWINGS

The invention will be described by way of example and with reference to the accompanying drawings in which.

DETAILED DESCRIPTION OF THE INVENTION

Figure 1A:
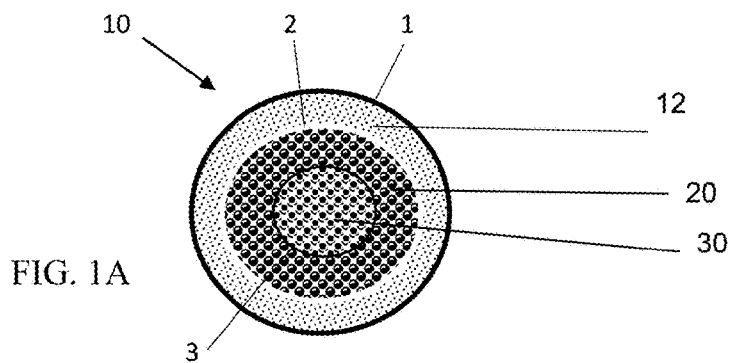
FIGS. 1A-1D are schematic cross-sectional microscopic views of the compositions shown as particles which make up the osteogenic scaffold.

With reference to FIGS. 1A-1D, the implantable osteogenic regenerative scaffold matrix composition for replacing necrotic bone is configured and dimensioned for insertion and to revascularize bone defects. The implantable scaffold matrix composition can be provided in a variety of forms, one type of which is shown in FIGS. 1A-1D. In this form, the composition 10 has three main ingredients, a polymer material 12, a pharmaceutical composition 20 and an organic material 30. In these compositions as shown in FIG. 1A, the implantable matrix composition can have a biodegradable inert coating or polymeric coating that covers the outside of the composition similar to a shell (1). Interior of the outer shell (1) of biodegradable inert coating material or of the polymer material 12 is a next layer (2) composed of a pharmaceutical composition 20 that can have a coating of a polymeric material or be impregnated with a polymeric material, that includes a time release of osteogenic effectors such as; ibuprofen, non-steroidal anti-inflammatory drugs (NSAIDS), acetaminophen, or naproxen sodium or any combination thereof Interior at the central core (3) is an organic material 30. The organic material 30 also coats a polymeric material 12 or is impregnated within a polymeric materials and has a time release of osteoclast inhibitors such as; hydroxamate-based matrix metalloproteinase (MMP) inhibitors, thiol-based MMP inhibitors, pyrimidine-based inhibitors, hydroxypyrone-based MMP inhibitors, phosphorus-based MMP inhibitors, tetracycline-based MMP inhibitors, and endogenous MMP inhibitors also known as tissue inhibitors of metalloproteinases (TIMPs). The names of some of these Galardin, Decorin, Actinonin, Marimastat, Batimastat, Ilomastat, Interleukin-1, oncostatin M, Tanomastat, Cipemastat, Rebimastat, phosphodiesterase type4 (PDE4) inhibitor, hydroxamate-based MMP inhibitors, MMI-270, MMI-166, ABT-770, RS-130830, compound 239796-97-5, compound 420121-84, compound 544678-85, Compound 556052-30-3, Ro 282653, compound 848773-43-3, compound 3-hydroxypyran-4-one also called 868368-30, metastat (also known as COL-3), Prinomastat, and Gelatinases, or any combination thereof. As shown, this particle composition is designed in such a way that the outer coating or shell (1) will be absorbed first then the next layer (2) then the interior core (3).

Figure 1B:
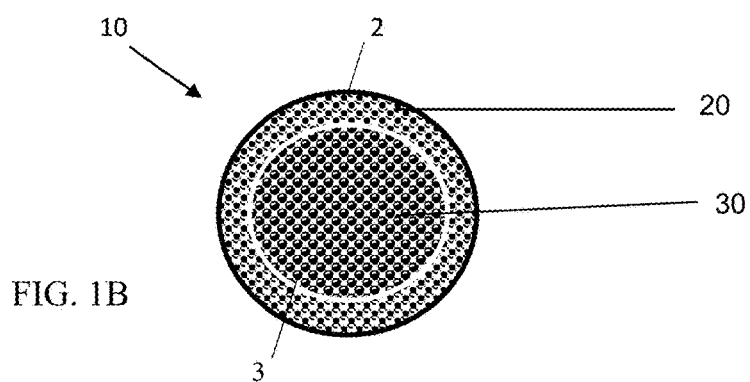

An alternative composition is shown in FIG. 1B wherein the osteogenic pharmaceutical material 20 is shown on the exterior layer (2) and the interior core (3) is the organic polymeric material 30. In this case the biodegradable coating (1) is optional.

Figure 1C:
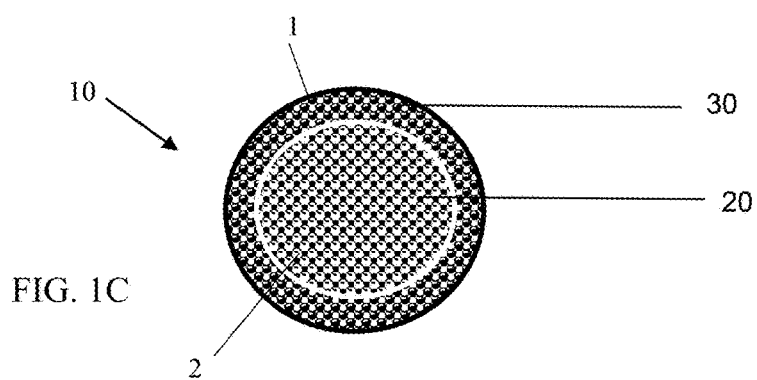

With reference to FIG. 1C, a reverse construction is shown where the exterior layer or core (3) is the organic polymeric material 30 on the exterior and the core or layer (2) is the pharmaceutical polymeric material 20.

Figure 1D:
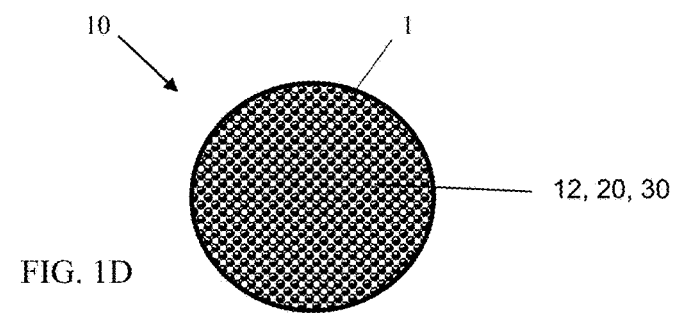

With reference to FIG. 1D, these materials can all be co-mixed together to make a homogenous composition 10 of the polymer material 12, pharmaceutical polymeric material 20, and organic polymer materials 30 in such a way as illustrated. In this case the biodegradable coating (1) is optional. In such a case, all these materials 12, 20 and 30 will release simultaneously over a period of time from 0 to 19 days.

Figure 2A:
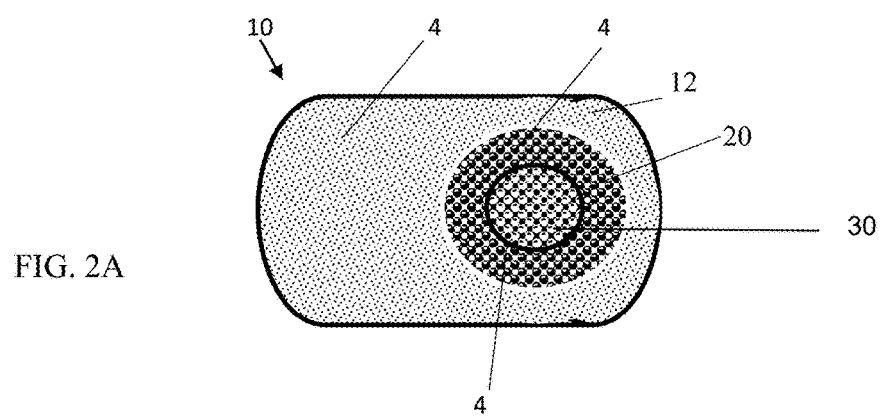
FIGS. 2A-2D are schematic cross-sectional macroscopic views of the compositions which form the structure of the osteogenic scaffold.
Figure 2B:
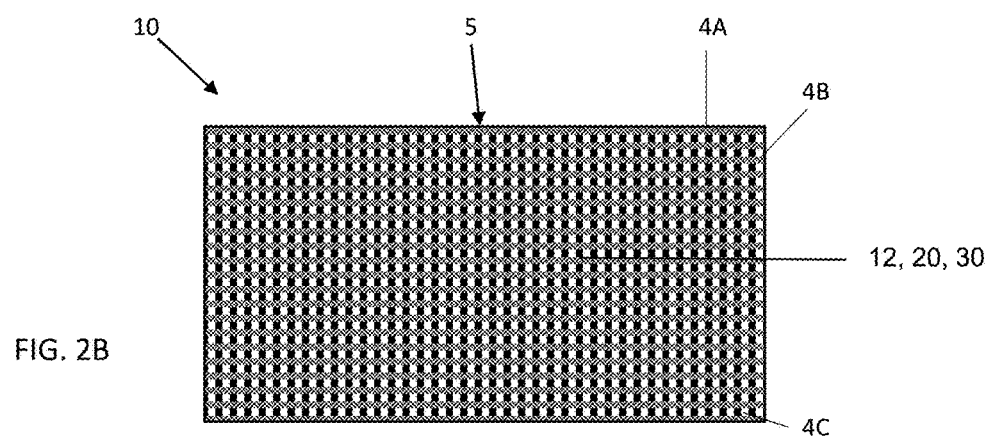
Figure 2C:
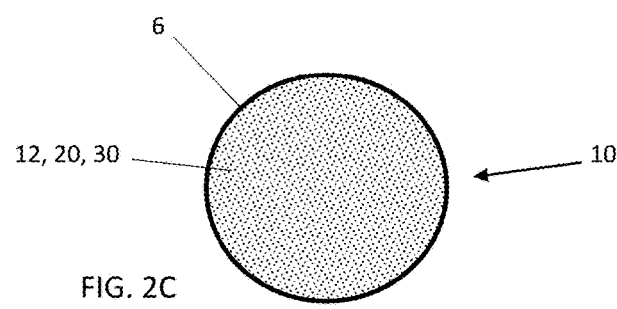
Figure 2D:
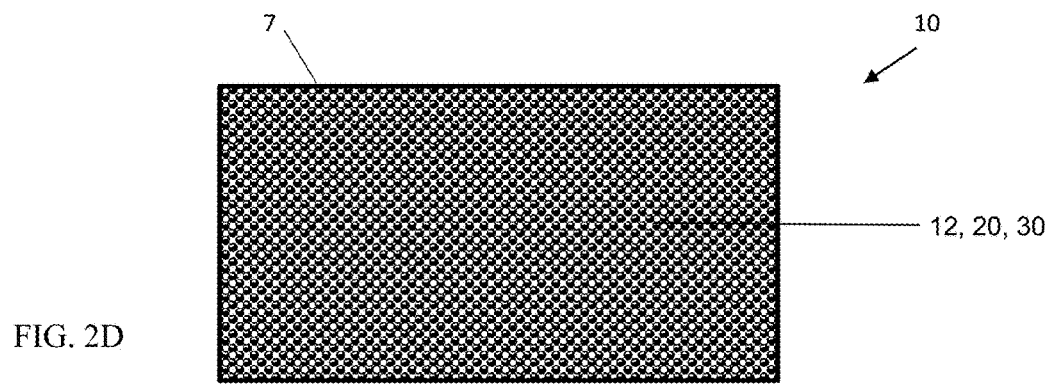

FIGS. 2A-2D are schematic cross-sectional macroscopic views of the compositions or materials 12, 20, 30 which form the structure of the osteogenic scaffold 4, FIG. 2A. The compositions 12, 20 or 30 may be formed into the shapes of fibers (4). FIG. 2B, multiple fibers 4A, 4B and 4C in a mesh conformation create an osteogenic regeneration scaffold (5). FIG. 2C, the compositions of materials 12, 20 and 30 may be formed into spheres (6). In FIG. 2D, multiple spheres in a spongy or porous conformation create an osteogenic regeneration scaffold (7).

Figure 3A:
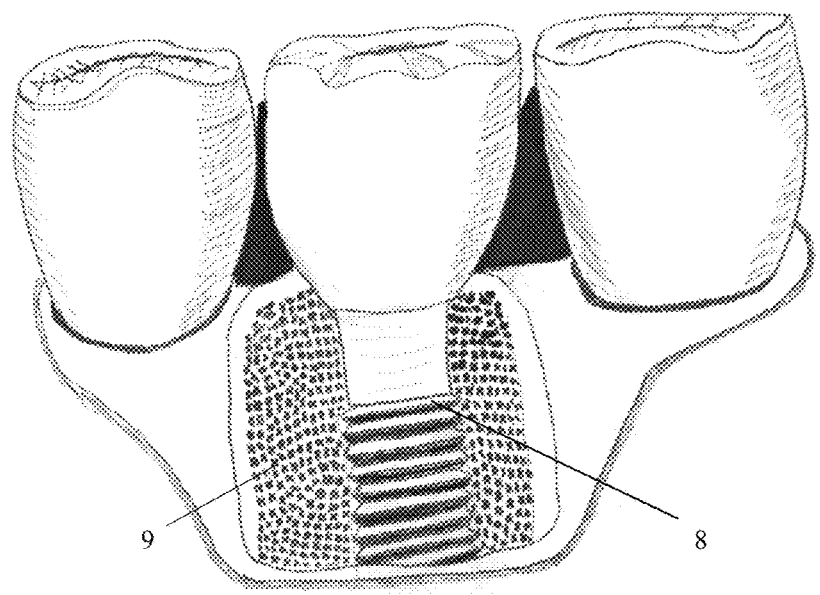
FIGS. 3A-3C are drawings of in a craniofacial bone defects which can be repaired using an osteogenic scaffold.
Figure 3B:
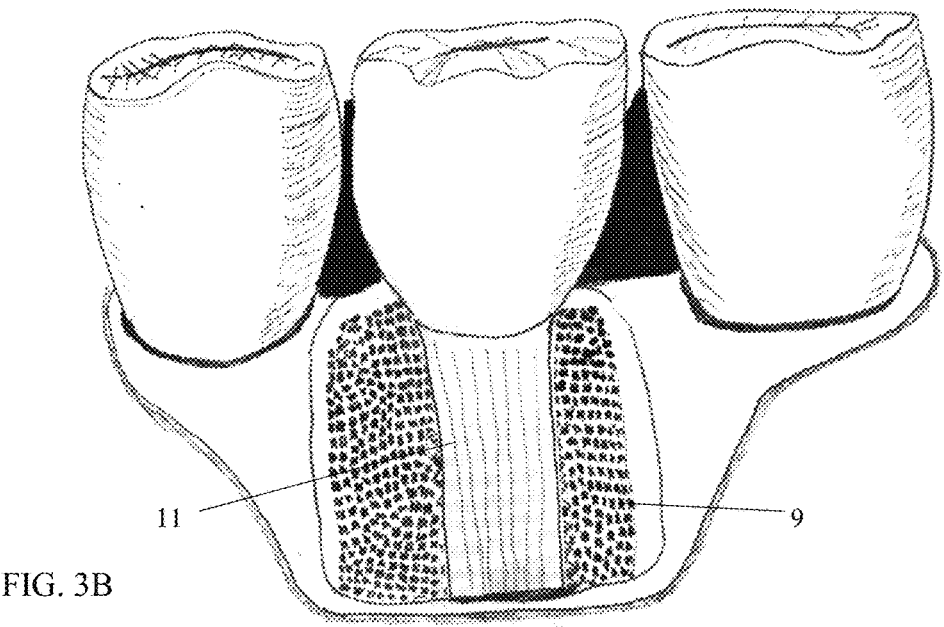
Figure 3C:
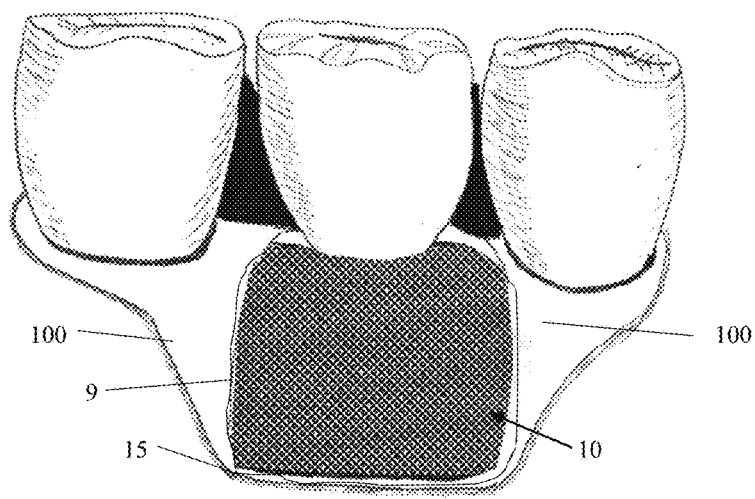

FIGS. 3A-3C are drawings of in a craniofacial bone defects which can be repaired using an osteogenic scaffold. FIG. 3A is a drawing of a dental implant (8) in a patient following peri-implantitis where supporting bone has been resorbed creating a bone defect (9). FIG. 3B is a drawing of a tooth root (11) in a patient after the supporting bone has been resorbed, creating a bone defect (9). FIG. 3C is a drawing of craniofacial bone defect site (9) filled with the osteogenic regeneration scaffold 10 described in this invention, and covered with a membrane 15 to separate the osteogenic scaffold 10 from the soft tissues 100.

Figure 4A:
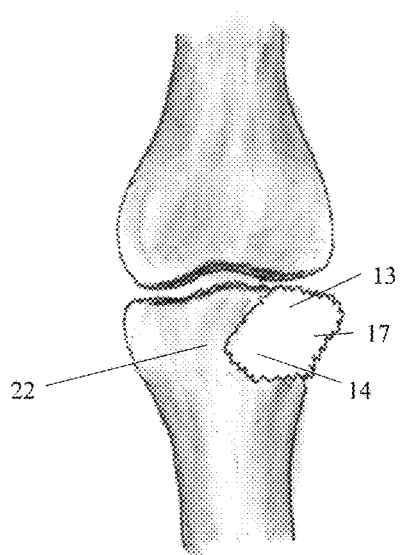
FIGS. 4A-4C are drawings of bone and joint defects which can be repaired using an osteogenic scaffold.
Figure 4B:
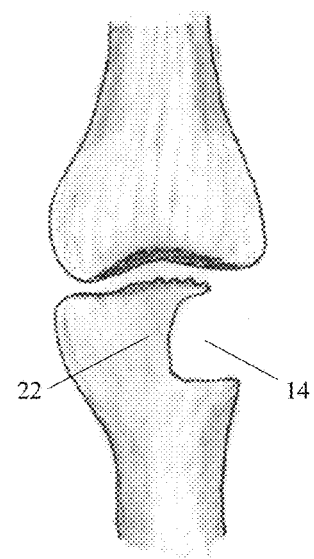
Figure 4C:
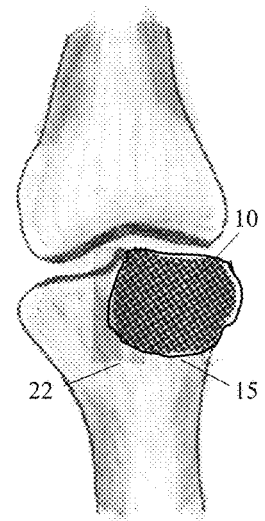

FIGS. 4A-4C are drawings of bone and joint defects which can be repaired using an osteogenic scaffold. FIG. 4A is a bone and/or joint defect site 14 containing injured, dead, necrotic or diseased tissue (13). FIG. 4B shows the debridement of dead or necrotic tissue 17 from the bone defect site (14) in preparation of receiving the osteogenic scaffold 10 of the present invention. FIG. 4C shows the bone defect site 14 filled with the osteogenic regeneration scaffold 10 described in this invention, and covered with a membrane 15 to separate the osteogenic scaffold 10 from the soft tissues 100.

Figure 5:
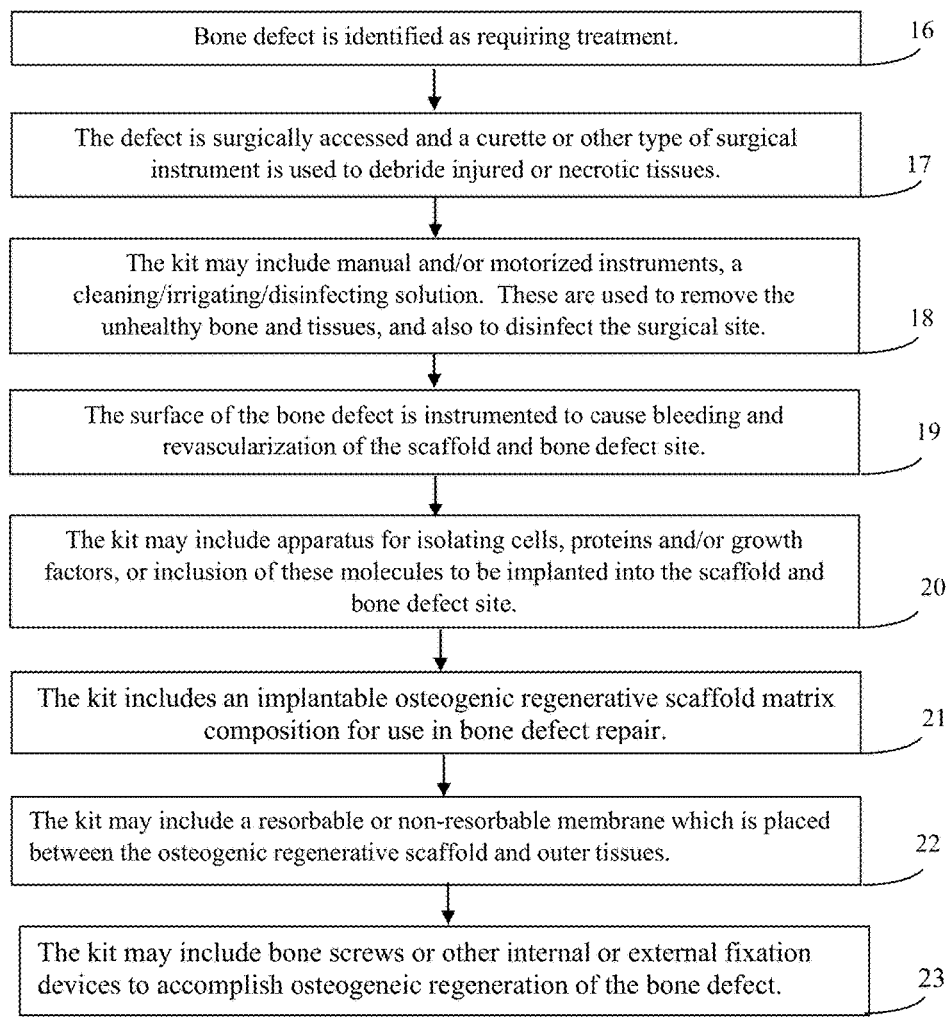
FIG. 5 is a description of the steps for using the osteogenic regeneration kit.

FIG. 5 is a description of the steps for using the osteogenic regeneration kit. The first step is to identify the bone defect (9, 14). The next step is to surgically access the defect site (9, 14) and use a curette or other type of surgical instrument is used to debride injured or necrotic tissues (17). The next step is to use manual and/or motorized instruments together with a cleaning/irrigating/disinfecting solution to remove the unhealthy bone and tissues 17, and also to disinfect the surgical defect site (9, 14). The next optional step is to instrument the surface of the bone defect 9, 14 to cause bleeding and revascularization of the scaffold and bone defect site (9, 14). The next optional step is to use apparatus for isolating cells, proteins and/or growth factors, or implant these molecules into the scaffold 10 and bone defect site (9, 14). The next step is to implant the osteogenic regenerative scaffold matrix composition 10 for use in bone defect repair. The next step is to cover the osteogenic regenerative scaffold 10 with a membrane 15 to separate the scaffold 10 from the outer tissues (22, 100). The next optional step is to use bone screws or other internal or external fixation devices to accomplish osteogeneic regeneration of the bone defect (9, 14).

Figure 6:
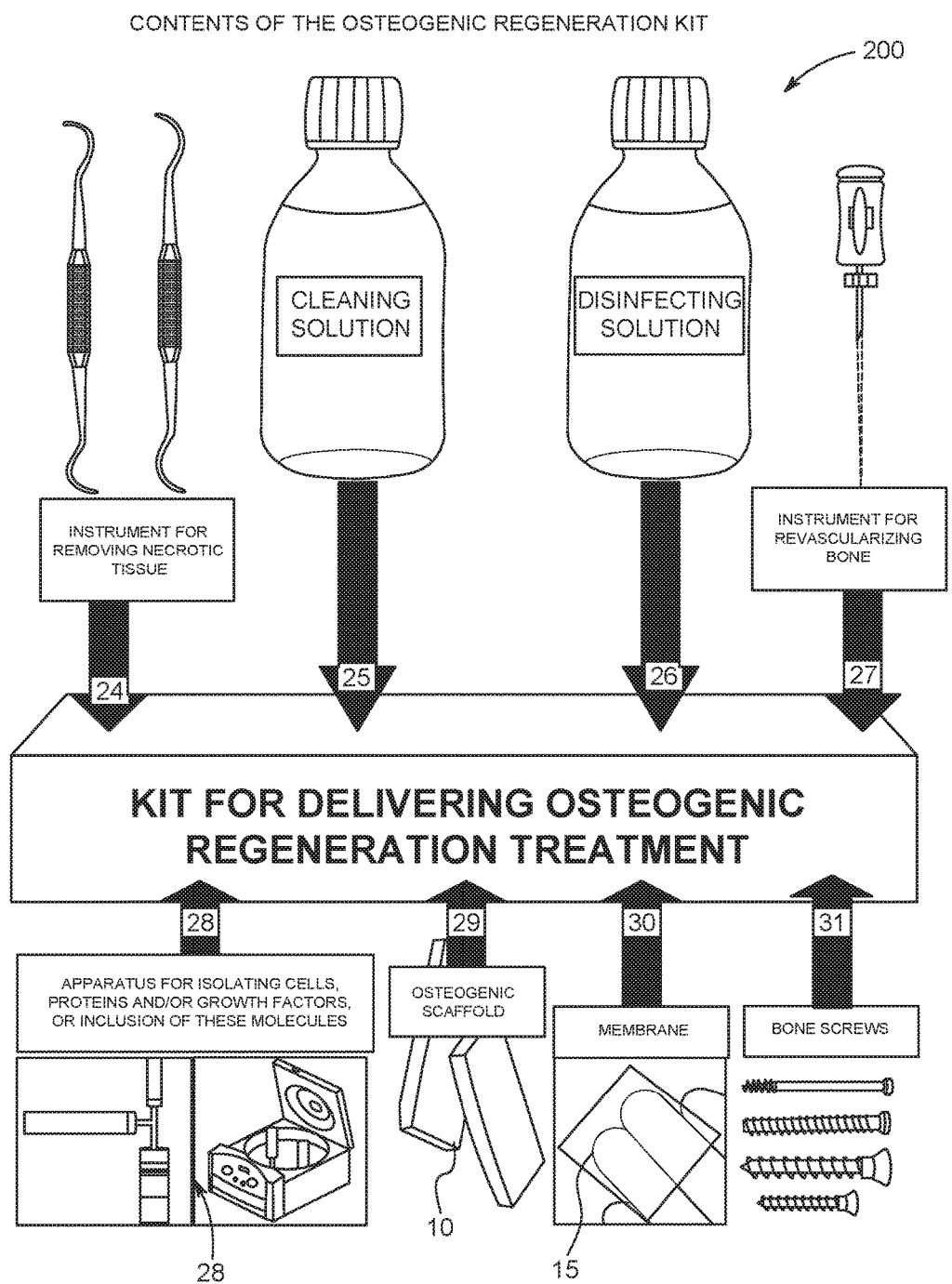
FIG. 6 is a view of an exemplary kit for osteogenic regeneration.

With reference to FIG. 6, an exemplary kit 200 for bone repair with an implantable osteogenic regenerative scaffold matrix composition of the present invention is shown. This kit 200 can include components for performing a regenerative osseogenic procedure to accomplish vascularized bone regeneration. The kit 200 may include instruments 24 for removing necrotic tissue. The kit 200 may include saline or other sterile wound cleaning solution 25. The kit 200 may include chlorhexidine or other wound disinfecting solution 26. The kit 200 may include an instrument 27 for revascularizing bone. The kit 200 may include apparatus 28 for isolating cells, proteins and/or growth factors, or inclusion of these molecules. The kit 200 includes a dose 29 of an osteogenic regenerative scaffold matrix composition 10 for use in bone defect repair. The kit 200 may include a resorbable or non-resorbable membrane 15 which is placed between the osteogenic regenerative scaffold 10 and outer tissues in a square or rectangular form (30). The kit 200 may include bone screws 31 or other internal or external fixation devices 31 to accomplish osteogeneic regeneration of the bone defect.

Figures 7, 8:
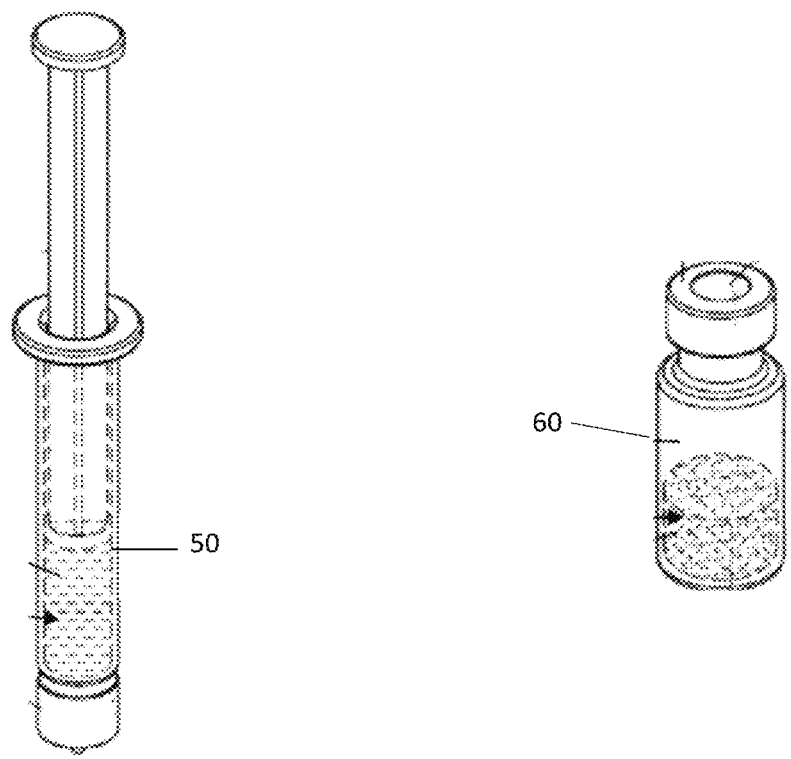
FIGS. 7 and 8 show platelet rich plasma, blood, or any blood serum product in the form of containers in the kit.

The implantable scaffold matrix can include platelet rich plasma, blood, or any blood serum product either in the form of containers 50, 60 in the kit or can be drawn directly from the patient to be treated and mixed with the scaffold matrix composition, as shown in FIGS. 7 and 8.

The revascularization instrument can be an ultrasonic instrument.

The kit can further include a disinfecting solution for removing bacteria.

The kit can further include a material selected from the group consisting of a biocompatible liner cement and an obturation material.

The implantable scaffold material can be a calcium phosphate, ceramic, or cement.

The implantable scaffold matrix can be a hydrogel material.

The revascularization instrument can be configured and dimensioned for enlarging the size of the bone defect.

The kit may further have isolated cells for use in the bone regeneration method. These isolated cells can be osteoblasts, progenitor cells, stem cells, cells from blood of periapical tissue, white blood cells.

The kit may include isolated cells that express at least one of von Willebrand factor CD146, alpha-smooth muscle actin, and 3G5 proteins. The kit may further include a cellular growth factor selected from the group consisting of one or more of a member of the transforming growth factor-beta family, a bone morphogenic protein, insulin-like growth factor-I, insulin-like growth factor-II, Colony stimulating factor, Epidermal growth factor, Fibroblast growth factor, any of Interleukins IL-1 to IL-13, Platelet-derived growth factor, Nerve growth factor, Estrogen (Estradiol), Testosterone, Progesterone, Gonadotropin-releasing hormone (GnRH), Insulin, Granulocyte-macrophage colony-stimulating factor (GM-CSF), Sphingosine-1-phosphate (S1P), Bone morphogenetic proteins 2 and 4 (BMP-2), (BMP-4), Transforming growth factor beta 1 (TGF-β1) or any combination thereof.

The kit can further have an organic composition selected from the group consisting of one or more osteoblast inhibitors: Galardin, Actinonin, Decorin, Actinonin, Marimastat, Batimastat and phosphodiesterase type4 (PDE4) inhibitor or any combination thereof. The kit can further have a pharmaceutical composition selected from the group consisting of one or more of ibuprofen, non-steroidal anti-inflammatory drugs (NSAIDs), Acetaminophen, or Naproxen sodium or any combination thereof.

Osteoclast function will be inhibited early and the osteoblastic function will kick in after that process. The important part of bone formation is early osteoclastic bone resorption and the creation of the cutting cones which occurs within the first few days and is very robust, followed by the recruitment of osteogenic progenitors that become osteoblasts and then repair of those cutting cones over several weeks and months. So the variable release is important to recapitulate the normal physiology of bone formation.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An implantable scaffold matrix composition for osteogenic regeneration, the scaffold comprises:

a biodegradable polymer material to promote osteoblast attachment;

a pharmaceutical composition to control local inflammation and includes osteogenic effectors;

an organic material for inhibiting the osteoclast resorption of bone; and wherein the composition is made as a particle composition configured having the biodegradable polymer material as an outer shell coating and covering the outside of the composition, interior of the biodegradable polymer is a layer made of the pharmaceutical composition and interior of the pharmaceutical composition is the organic material as an interior core, the particle composition having a time release wherein the outer coating is absorbed first, then the next layer, then the interior core wherein the polymer material, the pharmaceutical composition and the organic material are sequentially released creating a primary release of the pharmaceutical composition and a secondary release of the polymer released over a time period from greater than 0-19 days, wherein osteoclast resorption is inhibited early and the osteoblastic attachment is initiated after the creation of cutting cones which occurs within the first few days followed by the recruitment of osteogenic progenitors that become osteoblasts to initiate repair the cutting cones over several weeks by the sequential release to recapitulate normal physiology of bone formation.

2. The implantable scaffold matrix composition for osteogenic regeneration of claim 1, wherein the polymer material is material selected from the group consisting of one or more of polylactic acid, polyglycolic acid, and polycaprolactone, or any combination thereof.

3. The implantable scaffold matrix composition for osteogenic regeneration of claim 1 wherein the pharmaceutical composition comprises drugs consisting of one or more of ibuprofen, non-steroidal anti-inflammatory drugs (NSAIDS), acetaminophen, or naproxen sodium or any combination thereof.

4. The implantable scaffold matrix composition for osteogenic regeneration of claim 1, wherein the organic material for inhibiting the osteoclast resorption of bone is selected from a group consisting of one or more of hydroxamate-based matrix metalloproteinase (MMP) inhibitors, thiol-based MMP inhibitors, Pyrimidine-based inhibitors, hydroxypyrone-based MMP inhibitors, phosphorus-based MMP inhibitors, tetracycline-based MMP inhibitors, and endogenous MMP inhibitors also known as tissue inhibitors of metalloproteinases (TIMPs), phosphodiesterase type 4 or any combination of osteoclast inhibitors.

5. The implantable scaffold matrix composition for osteogenic regeneration of claim 1 wherein each time release extends between 0 days and 19 days, both not being at 0 days.

* * * * *